US010215699B2

(12) United States Patent
Cai et al.

(10) Patent No.: US 10,215,699 B2
(45) Date of Patent: Feb. 26, 2019

(54) UTILIZING UPDRAFT FLOW IN A FAN-LESS DUST SENSOR

(71) Applicant: Honeywell International Inc., Morris Plains, NJ (US)

(72) Inventors: Kevin Cai, Shanghai (CN); Ouyang Yang, Shanghai (CN); Anna Liu, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/397,527

(22) Filed: Jan. 3, 2017

(65) Prior Publication Data

US 2018/0188169 A1 Jul. 5, 2018

(51) Int. Cl.
*G01N 21/00* (2006.01)
*G01N 21/51* (2006.01)
*G01N 21/94* (2006.01)
*G01N 15/06* (2006.01)
*G01N 15/14* (2006.01)
*G01N 15/00* (2006.01)

(52) U.S. Cl.
CPC ............ *G01N 21/51* (2013.01); *G01N 15/06* (2013.01); *G01N 15/1459* (2013.01); *G01N 21/94* (2013.01); *G01N 2015/0003* (2013.01); *G01N 2015/0046* (2013.01); *G01N 2015/0693* (2013.01); *G01N 2015/1486* (2013.01); *G01N 2201/0612* (2013.01)

(58) Field of Classification Search
CPC ............... G01N 21/94; G01N 15/0205; G01N 2001/2282; G01N 21/3504; G01N 21/05; G01N 21/61

USPC ................................. 356/337–338, 437–439
See application file for complete search history.

(56) References Cited

U.S. PATENT DOCUMENTS 5,363,199 A * 11/1994 Victor .................. G01N 21/534
250/573
5,426,501 A 6/1995 Hokanson et al.
(Continued)

FOREIGN PATENT DOCUMENTS

CN         1800820 A      7/2006
CN       104316443 A      1/2015
(Continued)

OTHER PUBLICATIONS

International Application No. PCT/CN2015/097546, International Search Report, dated Sep. 6, 2016, 4 pages.
(Continued)

*Primary Examiner* — Isiaka O Akanbi
(74) *Attorney, Agent, or Firm* — Seager, Tufte & Wickhem LLP

(57) ABSTRACT

Embodiments relate to systems and methods for providing airflow within a particulate matter sensor. A particulate matter sensor may comprise an air duct, a light source configured to pass light through the air duct, a extender connected to the light source configured to dissipate thermal energy generated by the light source, and to generate a updraft of airflow into the air duct, a photodetector located in the air duct, and a computing device coupled to the photodetector. The computing device has a processor and a memory storing instructions which, when executed by the processor, determines a mass concentration of particles in the air duct based on an output of the photodetector.

18 Claims, 1 Drawing Sheet

(56) References Cited

U.S. PATENT DOCUMENTS

| | | | |
|---|---|---|---|
| 6,368,560 B1* | 4/2002 | Ostrander | G01N 21/05 356/432 |
| 6,447,583 B1* | 9/2002 | Thelen | B01D 53/06 95/113 |
| 8,243,274 B2 | 8/2012 | Aiken et al. | |
| 2004/0159799 A1 | 8/2004 | Saccomanno | |
| 2006/0119851 A1* | 6/2006 | Bounaix | G01N 21/031 356/437 |
| 2008/0246965 A1 | 10/2008 | Miller | |

FOREIGN PATENT DOCUMENTS

| WO | 2016065465 A1 | 5/2016 |
|---|---|---|
| WO | 2017101038 A1 | 6/2017 |

OTHER PUBLICATIONS

International Application No. PCT/CN2015/097546, Written Opinion of the International Searching Authority, dated Sep. 6, 2016, 4 pages.

Samyoung S&C Co., Ltd, DSM501, Dust Sensor Module [retrieved on Jul. 13, 2017]. Retrieved from the Internet< URL: http://www.google.com/url?sa=t&rct=j&q=&esrc=s&source=web&cd=2&cad=rja&uact=8&ved=0ahUKEwj02riT26nRAhUD7oMKHUCKC_cQFggfMAE&url=http%3A%2F%2Fwww.samyoungsnc.com%2Fproducts%2F3-1%2520Specification%2520DSM501.pdf&usg=AFQjCNHVHMpQrJrXle3RwiViQkhzMvvd3Q>, 11 pages.

\* cited by examiner

UTILIZING UPDRAFT FLOW IN A FAN-LESS DUST SENSOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

A particulate matter sensor or dust sensor may be used to determine a quality of air, for example in a quality of air that is input to and/or output from an air cleaner. In some industrialized regions, environmental air may have high concentrations of particulate matter of different sizes. If the concentration of such particulate matter is high enough, it may be deleterious to human health. Consumers may wish to purchase and install air cleaners for the residences to improve the quality of air breathed in the home. Such consumer grade air cleaners may desirably be modestly priced and compact in size.

SUMMARY

In an embodiment, a particulate matter sensor may comprise an air duct; a light source; a extender connected to the light source configured to dissipate thermal energy generated by the light source, and configured to generate a updraft of airflow into the air duct; a photodetector located in the air duct; and a computing device coupled to the photodetector having a processor and a memory storing instructions which, when executed by the processor, determines a mass concentration of particles in the air duct based on an output of the photodetector.

In an embodiment, a method for determining the concentration of particulate matter within an environment may comprise allowing ambient air to enter a particulate matter sensor; powering a light source within the particulate matter sensor; dissipating heat from the light source via an extender connected to the light source; generating an updraft into an air duct within the particulate matter sensor via the dissipated heat rising into the air duct; directing the light source through the air duct; detecting, by a photodetector, light scattered off of particulate matter in the air duct; and determining a mass concentration of particles in the air duct based on an output of the photodetector.

In an embodiment, a particulate matter sensor may comprise an air duct; a laser diode; a extender connected to the laser diode, located near an inlet to the air duct, and configured to generate a updraft of airflow into the air duct; a photodetector located in the air duct; and a computing device coupled to the photodetector having a processor and a memory storing instructions which, when executed by the processor, determines a mass concentration of particles in the air duct based on an output of the photodetector.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
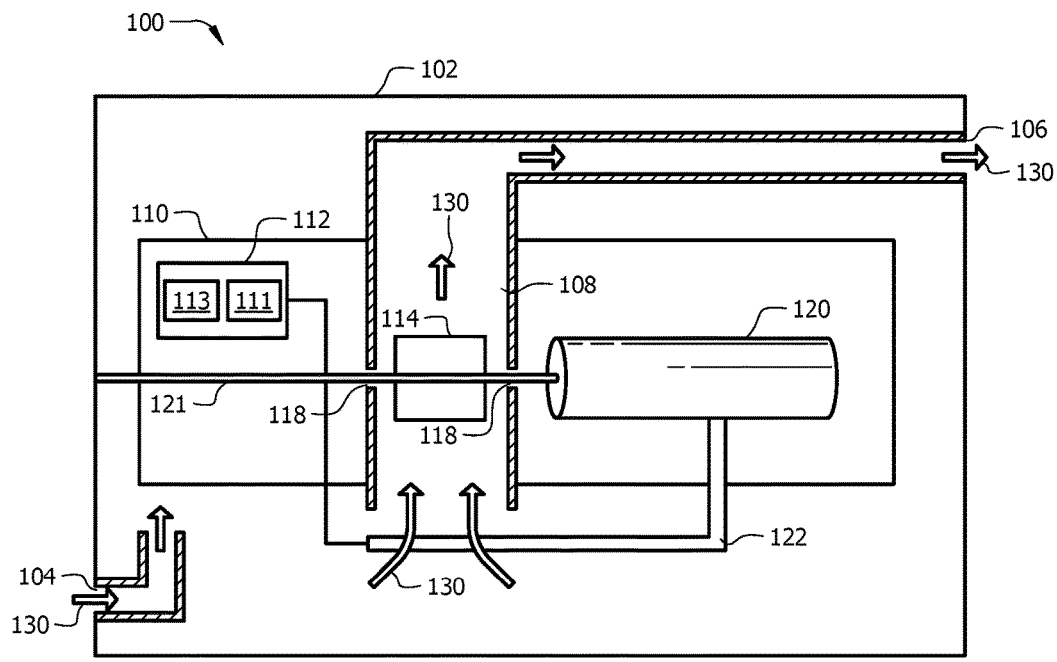
FIG. 1 illustrates a schematic diagram of a particulate matter sensor according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can" "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for providing air flow in a particulate matter (or dust) sensor. Typical dust sensors can provide good accuracy, consistency and fairly acceptable manufacturing cost using a fan to generate air flow within the sensor. However, there's a demand to remove the fan inside the sensor to eliminate the noise created by the fan and to increase the use lifetime of the sensor. Additionally, from a cost perspective, removing the fan component may cut down the bill of materials (BOM) cost (approximately 30%).

A challenge for providing a fan-less dust sensor is that the small particulate matter detection system loses a well-managed air introduction mechanism (i.e. the fan) to provide a constant airflow through the detection area, thus rendering a bad statistical effect for moving particles in the air.

Embodiments of the disclosure provide a fan-less dust sensor comprising a method for generating airflow within the sensor based on dissipation of thermal energy. The disclosed embodiments may provide airflow without significantly increasing cost or impacting performance of the sensor. The disclosure suggests a new way of generating an active airflow inside the dust sensor using a heat source. When heated, the air near the heat source will tend to drift up, forming an updraft in a limited space due to a conspicuous temperature difference (which is known as convective flow). With such an active flow control, particles in the air can orderly enter the detection area, where a beam of light passes through the detection area and the scattered light signals caused by particles hitting the beam can be received by a photodetector. The orderly airflow, generated by the heat source, through the detection area may guarantee an acceptable sampling effect without the use of a fan in the sensor.

One possible source of heat (or thermal energy) that may be used is the light source in the sensor. In some sensors, the light source may comprise a laser module (or laser diode). The laser module may comprise an extended metal piece attached to a copper housing of the laser diode, and the extender may be configured to dissipate the heat created by the laser diode. When the laser diode has been powered on for a certain amount of time, the temperature of the extender may rise up to approximately 45° C. The metal extender may also serve as an extra heat sink to help cool the laser diode.

The sensor housing may comprise a carefully designed air duct or fluid channel to direct airflow within the sensor. A bent inlet at one side of the sensor housing may allow ambient air to enter the sensor, while the bend or angle enthralls larger particles or dust. A bent outlet at the top of the air duct may prevent particles from falling back to the laser beam for a second time. Also the height of the duct is carefully designed to ensure most of the particles exit the sensor housing. Additionally, the bends or angles in the inlet and outlet may prevent any light from the light source from escaping the interior of the sensor. The air duct may comprise two small holes for the beam to penetrate the air duct perpendicularly without any hindrance.

An onboard microprocessor may monitor the heat source temperature (of the extender) and the ambient temperature. When the dimensions and material of the air duct are know, the temperature difference may be used to determine the airflow velocity within the air duct. The microprocessor may calculate the current airflow velocity per temperature difference and a preset velocity, and may then calculate the correct the mass concentration of particulate matter in the airflow based on one or more algorithms. By removing the need for a fan within the sensor, mechanical noise from the fan may be completely removed. Additionally, a failure point is removed by removing the fan, thereby improving the lifetime of the sensor.

FIG. 1 illustrates an exemplary particulate matter sensor 100 comprising a laser diode 120. The laser diode 120 may comprise an extender 122, where the extender 122 may comprise an extended metal rod, plate, or other thermally conductive element attached to the housing of the laser diode 120. The extender 122 may be configured to conduct heat from the laser diode 120 to allow the thermal energy that is generated by the laser diode 120 to be dissipated away from the laser diode 120. The extender 122 may comprise a thermally conductive material such as a metal material, thermally conductive polymer, or the like that is thermally coupled to a metal housing of the laser diode 120.

The extender 122 may be positioned near the opening of an air duct 108 within a housing 102 of the sensor 100. The shape of the extender 122 near the opening can be any suitable shape that allows for heat transfer of the thermal energy from the extender 122 to the air. In some embodiments, the extender 122 can be in the shape of a rod or plate, or a series of rods or plates. In some embodiments, the extender 122 can be in the form of fins having open or closed channel flow near the opening of the air duct 108. While shown as being located at or near the opening of the air duct 108, the extender 122 can be located within the channel or even the outlet of the air duct 108, depending on the shape of the duct 108, to provide a similar airflow pattern and volumetric flowrate.

The air duct 108 may be shaped to direct the airflow 130 within the housing 102. The housing 102 may comprise an inlet 104 and an outlet 106. Airflow 130 may enter the housing 102 via the inlet 104. The inlet 104 may comprise an angle or bend, configured to withstand turbulence and block larger particles. The thermal energy dissipated by the extender 122 may heat the air and generate an updraft into the air duct 108, wherein the airflow 130 may be pulled into the air duct 108 toward the outlet 106. The outlet 106 may comprise an angle or bend, configured to reduce the chances of particles falling back down the air duct 108, causing a second-time detection and an error in the readings.

The air duct 108 can have a consistent shape within the area surrounding the photodetector 114 (e.g., in a central region). For example the air duct 108 can have a constant cross-sectional area in the central region. In some embodiments, other shapes can be used. For example, the air duct 108 may narrow near the central region to increase the velocity of the airflow. In some embodiments, the air duct 108 may widen near the central region to reduce the velocity over the photodetector 114, which may be beneficial to produce a laminar flow, depending on the volumetric flowrate.

The laser diode 120 may generate a beam 121 that passes through the air duct 108. In some embodiments, the beam 121 of light can be collimated and/or focused. It is noted that embodiments of the present disclosure do not limit the laser 120 to a particular type of laser. Additionally, though one laser 120 is shown, embodiments of the present disclosure can utilize more than one laser. The sensor 100 may comprise a photodetector 114, which may be located near and/or adjacent to the air duct 108. The photodetector 114 is a device that receives one or more light signals and transforms the light signal(s) into electronic signal(s). Embodiments of the present disclosure do not limit the photodetector 114 to a particular type of photodetector.

Particulate matter in the airflow 130, which may also be referred to as "dust," can enter the air duct 108. Thereafter, the dust can travel into a path of the beam 121 of the laser 120. The light of the laser beam 122 may scatter and/or reflect off of the dust in the airflow 130. The scattered light signals can be received by the photodetector 114, and the photodetector 114 can transform the scattered light signals into electronic signals.

In some embodiments, the laser diode 120, the extender 122, and/or the photodetector 114 can be controlled by a computing device (e.g., microprocessor) 112. In some embodiments, the laser 120, photodetector 114 and/or computing device 112 may be located on a printed circuit board (PCB) 110.

The computing device 112 can execute instructions (e.g., implemented as software and/or firmware) to control the laser 120, the extender 122, and/or the photodetector 108. Further, as discussed herein, the computing device 112 can convert the electronic signals received from the photodetector 114 to determined mass concentration of the dust in the airflow 130. The computing device 112 can generate a display of the determined mass concentration. That is, in some embodiments, the sensor 100 can include a display configured to display a determined mass concentration of dust.

The computing device 112 can include a memory 111. The memory 111 can be any type of storage medium that can be accessed by a processor 113 to perform various examples of the present disclosure. For example, the memory 111 can be a non-transitory computer readable medium having computer readable instructions (e.g., computer program instructions) stored thereon that are executable by the processor 113 to receive a number of electronic signals.

The memory 111 can be volatile or nonvolatile memory. The memory 111 can also be removable (e.g., portable) memory, or non-removable (e.g., internal) memory. For example, the memory 111 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical storage, and/or a magnetic medium such as magnetic cassettes, tapes, or disks, among other types of memory.

Further, although the memory 111 is illustrated as being located within the computing device 112, embodiments of the present disclosure are not so limited. For example, the memory 111 can also be located internal to another computing resource (e.g., enabling computer readable instructions to be downloaded over the Internet or another wired or wireless connection).

As previously discussed, the computing device 112 can receive electronic signals from the photodetector 114. In some embodiments, the computing device 112 can receive a first plurality of electronic signals from the photodetector 114 over a particular period of time, the first plurality of electronic signals associated with a first plurality of particles, wherein each of the first plurality of signals has a respective amplitude. An analog to digital converter (ADC) can be located on the same PCB 110 as the photodetector 114, for instance, and can sample the electronic signals.

The extender 122 that provides the heat source may be manufactured with a thermally conductive material such as copper to provide a high rate of thermal conduction. The airflow within the air duct 108 may be measured with respect to a standard ambient environment of 25° C. and 50% relative humidity. Using those known quantities, the computing device 112 may measure the temperature difference between the heat source (extender 122) and the ambient environment to determine real-time airflow rates.

Figure 2:
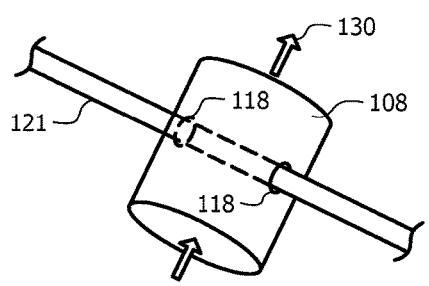
FIG. 2 illustrates a perspective view of an air duct within a particulate matter sensor according to an embodiment of the disclosure.

FIG. 2 illustrates a perspective view of the air duct 108, with the beam 121 from the laser diode 120 passing through the openings 118 in the air duct 108. The openings 118 may be shaped to allow the laser to pass through the air duct 108, while not allowing a significant amount of airflow and/or particles to pass through the openings 118. The air duct 108 may comprise a cylindrical shape. In other embodiments, the air duct 108 may comprise rectangular, oval, elliptical, or other three-dimensional shapes.

In a first embodiment, a particulate matter sensor may comprise an air duct; a light source; a extender connected to the light source configured to dissipate thermal energy generated by the light source, and configured to generate a updraft of airflow into the air duct; a photodetector located in the air duct; and a computing device coupled to the photodetector having a processor and a memory storing instructions which, when executed by the processor, determines a mass concentration of particles in the air duct based on an output of the photodetector.

A second embodiment can include the particulate matter sensor of the first embodiment, wherein the light source is a laser diode.

A third embodiment can include the particulate matter sensor of the first or second embodiments, wherein at least a portion of the extender is located near an inlet of the air duct.

A fourth embodiment can include the particulate matter sensor of the third embodiment, wherein the photodetector is located downstream of the inlet of the air duct.

A fifth embodiment can include the particulate matter sensor of any of the first to fourth embodiments, wherein the photodetector is configured to detect light scattered off of particulate matter in the airflow in the air duct.

A sixth embodiment can include the particulate matter sensor of any of the first to fifth embodiments, wherein the sensor is a dust sensor.

A seventh embodiment can include the particulate matter sensor of any of the first to sixth embodiments, wherein the computing device determines an airflow rate within the air duct based on a temperature of the extender.

In an eighth embodiment, a method for determining the concentration of particulate matter within an environment may comprise allowing ambient air to enter a particulate matter sensor; powering a light source within the particulate matter sensor; dissipating heat from the light source via an extender connected to the light source; generating an updraft into an air duct within the particulate matter sensor via the dissipated heat rising into the air duct; directing the light source through the air duct; detecting, by a photodetector, light scattered off of particulate matter in the air duct; and determining a mass concentration of particles in the air duct based on an output of the photodetector.

A ninth embodiment can include the method of the eight embodiment, wherein at least a portion of the extender is positioned near an inlet of the air duct.

A tenth embodiment can include the method of the ninth embodiment, wherein the photodetector is positioned downstream of the inlet of the air duct.

An eleventh embodiment can include the method of any of the eighth to tenth embodiments, wherein the light source comprises a laser diode.

A twelfth embodiment can include the method in of any of the eighth to eleventh embodiments, further comprising controlling the elements of the particulate matter sensor via a computing device.

A thirteenth embodiment can include the method of any of the eighth to twelfth embodiments, wherein determining the mass concentration of particles in the air duct is completed by a computing device connected to the photodetector.

A fourteenth embodiment can include the method of any of the eighth to thirteenth embodiments, further comprising determining the airflow rate within the air duct.

A fifteenth embodiment can include the method of the any of the eighth to fourteenth embodiments, further comprising determining an airflow rate within the air duct based on a temperature difference between a temperature of the extender and a temperature of the ambient air.

In a sixteenth embodiment, a particulate matter sensor may comprise an air duct; a laser diode; a extender connected to the laser diode, located near an inlet to the air duct, and configured to generate a updraft of airflow into the air duct; a photodetector located in the air duct; and a computing device coupled to the photodetector having a processor and a memory storing instructions which, when executed by the processor, determines a mass concentration of particles in the air duct based on an output of the photodetector.

A seventeenth embodiment can include the particulate matter sensor of the sixteenth embodiment, wherein the extender is further configured to dissipate thermal energy from the laser diode, thereby generating the updraft of airflow.

An eighteenth embodiment can include the particulate matter sensor of the sixteenth or seventeenth embodiments, wherein the photodetector is located downstream of the inlet of the air duct.

A nineteenth embodiment can include the particulate matter sensor of any of the sixteenth to eighteenth embodiments, further comprising a housing; an inlet to the housing, wherein the inlet comprises an angled air flow channel; and an outlet to the housing, wherein the outlet comprises an angled air flow channel.

A twentieth embodiment can include the particulate matter sensor of the nineteenth embodiment, wherein the angled air flow channel is configured to block light from the light source from exiting the housing.

A twenty-first embodiment can include the particulate matter sensor and/or method of any of the first to twentieth embodiments, wherein the airflow within the sensor (i.e. within the air duct of the sensor) is generated without the use of a fan.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A particulate matter sensor comprising:
    an air duct;
    a light source configured to pass a light beam into the air duct;
    an extender, offset from the light beam but connected to the light source, conducting thermal energy generated by the light source to heat air to generate a convective induced airflow in the air duct;
    a photodetector configured to detect light of the light beam that is scattered and/or reflected off of particulate matter in the airflow in the air duct; and
    a computing device coupled to the photodetector having a processor and a memory storing instructions which, when executed by the processor, determines a mass concentration of particles in the air duct based on an output of the photodetector.

2. The particulate matter sensor of claim 1, wherein the light source is a laser diode.

3. The particulate matter sensor of claim 1, wherein at least a portion of the extender is located near an inlet of the air duct.

4. The particulate matter sensor of claim 3, further comprising a printed circuit board and an analog to digital converter; wherein the photodetector is located downstream of the inlet of the air duct; wherein the analog to digital converter, the light source, the photodetector, and the computing device are positioned on the printed circuit board.

5. The particulate matter sensor of claim 1, wherein the sensor is a dust sensor.

6. The particulate matter sensor of claim 1, wherein the computing device determines an airflow rate within the air duct based on a temperature of the extender.

7. A method for determining the concentration of particulate matter within an environment, the method comprising:
   allowing ambient air to enter a particulate matter sensor;
   powering a light source within the particulate matter sensor to generate a light beam in an air duct;
   dissipating heat produced by the light source through an extender that extends from the light source to produce a convective induced airflow within the air duct;
   directing the light beam into the airflow within the air duct;
   detecting, by a photodetector, light scattered or reflected off of particulate matter in the airflow within the air duct; and
   determining a mass concentration of particles in the airflow within the air duct based on an output of the photodetector.

8. The method of claim 7, wherein the photodetector is positioned downstream of the inlet of the air duct.

9. The method of claim 7, further comprising determining an airflow rate within the air duct based on a temperature difference between a temperature of the extender and a temperature of the ambient air.

10. The method of claim 7, wherein the light source comprises a laser diode.

11. The method of claim 7, further comprising controlling the elements of the particulate matter sensor via a computing device.

12. The method of claim 7, wherein determining the mass concentration of particles in the air duct is completed by a computing device operatively connected to the photodetector.

13. The method of claim 7, further comprising determining the airflow rate within the air duct.

14. A particulate matter sensor comprising:
   an air duct;
   a laser diode configured to generate a light beam and to direct the light beam into the air duct;
   an extender offset from the light beam, the extender thermally connected to the laser diode extending to a location near an inlet of the air duct, wherein the extender is configured to transfer heat generated by the laser diode to the location near the inlet of the air duct to produce a convective updraft of airflow into the air duct;
   a photodetector configured to detect light of the light beam that is scattered and/or reflected off of particulate matter in the airflow in the air duct; and
   a computing device coupled to the photodetector having a processor and a memory storing instructions which, when executed by the processor, determines a mass concentration of particles in the air duct based on an output of the photodetector.

15. The particulate matter sensor of claim 14, wherein the extender is further configured to dissipate thermal energy from the laser diode.

16. The particulate matter sensor of claim 14, wherein the photodetector is located downstream of the inlet of the air duct.

17. The particulate matter sensor of claim 14, further comprising:
   a housing;
   an inlet to the housing, wherein the inlet comprises an angled air flow channel; and
   an outlet to the housing, wherein the outlet comprises an angled air flow channel.

18. The particulate matter sensor of claim 17, wherein the angled air flow channel is configured to block light from the light source from exiting the housing.

* * * * *